(12) United States Patent
Machida et al.

(10) Patent No.: US 11,464,956 B2
(45) Date of Patent: Oct. 11, 2022

(54) MICRONEEDLE DEVICE

(71) Applicant: HISAMITSU PHARMACEUTICAL CO., INC., Tosu (JP)

(72) Inventors: Kazuya Machida, Tokyo (JP); Shinpei Nishimura, Tsukuba (JP); Seiji Tokumoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 227 days.

(21) Appl. No.: 16/488,456

(22) PCT Filed: Feb. 20, 2018

(86) PCT No.: PCT/JP2018/005981
§ 371 (c)(1),
(2) Date: Aug. 23, 2019

(87) PCT Pub. No.: WO2018/155433
PCT Pub. Date: Aug. 30, 2018

(65) Prior Publication Data
US 2019/0374761 A1    Dec. 12, 2019

(30) Foreign Application Priority Data
Feb. 24, 2017  (JP) .............................. JP2017-033775

(51) Int. Cl.
*A61M 37/00*  (2006.01)
*A61K 9/00*   (2006.01)
*A61K 9/70*   (2006.01)

(52) U.S. Cl.
CPC ....... *A61M 37/0015* (2013.01); *A61K 9/0021* (2013.01); *A61K 9/703* (2013.01);
(Continued)

(58) Field of Classification Search
CPC ...... A61M 37/0015; A61M 2037/0023; A61M 2037/0053; A61M 2037/0061; A61M 37/00; A61K 9/0021; A61K 9/703
See application file for complete search history.

(56) References Cited

U.S. PATENT DOCUMENTS

2006/0177494 A1* 8/2006 Cormier ............ A61M 37/0015
                                                424/449
2006/0275170 A1* 12/2006 Ameri .................... A61L 2/087
                                                53/425
(Continued)

FOREIGN PATENT DOCUMENTS

CN     101102809 A     1/2008
CN     102264429 A    11/2011
(Continued)

OTHER PUBLICATIONS

Vinardell et al., "Alternative Methods for Eye and Skin Irritation Tests: An Overview", Jan. 2006, Journal of Pharmaceutical Sciences, vol. 97, No. 1, pp. 46-59. (Year: 2006).*
(Continued)

*Primary Examiner* — Amber R Stiles
(74) *Attorney, Agent, or Firm* — Nath, Goldberg & Meyer; Joshua B. Goldberg

(57) ABSTRACT

A microneedle device of the present invention comprises a substrate, microneedles disposed on the substrate, and a coating layer formed on the microneedles, wherein a length of the microneedles is 300 to 500 μm, the microneedles are disposed on the substrate at a density of 28 to 80 needles/cm$^2$, and the coating layer comprises a biologically active substance. The microneedle device allows the skin irritation caused by administration of an agent to be reduced.

3 Claims, 3 Drawing Sheets

(52) U.S. Cl.
CPC ............ *A61M 2037/0023* (2013.01); *A61M 2037/0053* (2013.01); *A61M 2037/0061* (2013.01)

(56) References Cited

U.S. PATENT DOCUMENTS

| | | | | |
|---|---|---|---|---|
| 2015/0305739 | A1* | 10/2015 | Rolandi | A61B 17/08 606/221 |
| 2016/0015952 | A1* | 1/2016 | Omachi | A61K 9/0021 424/444 |
| 2019/0009070 | A1* | 1/2019 | Fudoji | A61M 37/00 |

FOREIGN PATENT DOCUMENTS

| | | |
|---|---|---|
| CN | 105311738 A | 2/2016 |
| JP | 2001-506904 A | 5/2001 |
| JP | 2008-528192 A | 7/2008 |
| JP | 201332324 A | 2/2013 |
| JP | 2013-177376 A | 9/2013 |
| JP | 2015-109963 A | 6/2015 |
| JP | 2015-523139 A | 8/2015 |
| JP | 2015173901 A | 10/2015 |
| KR | 20160125405 A | 10/2016 |
| TW | 201043278 A1 | 12/2010 |
| WO | 98/28037 A1 | 7/1998 |
| WO | 2006083681 A2 | 8/2006 |
| WO | 2010059605 A1 | 5/2010 |
| WO | 2011148994 A1 | 12/2011 |
| WO | 2013188884 A1 | 12/2013 |
| WO | 2015136639 A1 | 9/2015 |

OTHER PUBLICATIONS

Japanese Office Action dated Oct. 27, 2020 corresponding to application No. P2019-501336.
Taiwanese Office Action dated Jan. 21, 2021 corresponding to Patent Application No. 107106078.
European Search Report dated Dec. 1, 2020 corresponding to application No. 18758313.3.
Taiwanese Office Action dated Jul. 9, 2020 corresponding to Patent Application No. 107106078.
Chinese Office Action dated Dec. 18, 2020 corresponding to application No. 201880007029.9.
Korean Office Action dated Jan. 8, 2021 corresponding to application No. 10-2019-7017849.
Japanese Office Action dated May 25, 2021 corresponding to application No. 2019-501336.

* cited by examiner

MICRONEEDLE DEVICE

This is a National Phase Application filed under 35 U.S.C. 371 as a national stage of PCT/JP2018/005981, filed Feb. 20, 2018, an application claiming the benefit of Japanese Application No. 2017-033775, filed Feb. 24, 2017, the content of each of which is hereby incorporated by reference in its entirety.

TECHNICAL FIELD

The present invention relates microneedle device.

BACKGROUND ART

Administration using a microneedle device is known as a form of administering an agent (for example, Patent Literature 1). A microneedle device allows microneedles to make punctures in a stratum corneum layer as the outermost layer of the skin so as to form fine holes through which an agent passes, so that the agent can be transdermally administered.

CITATION LIST

Patent Literature

Patent Literature 1: Japanese Unexamined Patent Publication No. 2001-506904

SUMMARY OF INVENTION

Technical Problem

Administration of an agent using a conventional microneedle device causes undesirable skin irritation such as pigmentation on the skin in rare cases.

Solution to Problem

Through intensive study, the present inventors have surprisingly found that even a microneedle device having the same amount of the same biologically active substance as with a conventional microneedle device allows the skin irritation to be reduced through control of the density of the microneedles in a specified range, and thereby accomplished the present invention.

The present invention relates to a microneedle device comprising a substrate, microneedles disposed on the substrate, and a coating layer formed on the microneedles, wherein a length of the microneedles is 300 to 500 μm, the microneedles are disposed on the substrate at a density of 28 to 80 needles/cm$^2$, and the coating layer comprises a biologically active substance.

The microneedle device may cause less skin irritation than microneedle devices having microneedles disposed on a substrate at a density of 156 to 640 needles/cm$^2$, and the skin irritation may be indicated by a primary irritation index of Draize method.

Advantageous Effects of Invention

According to the microneedle device of the present invention, skin irritation caused by administration of an agent can be reduced.

DESCRIPTION OF EMBODIMENTS

Figure 1:
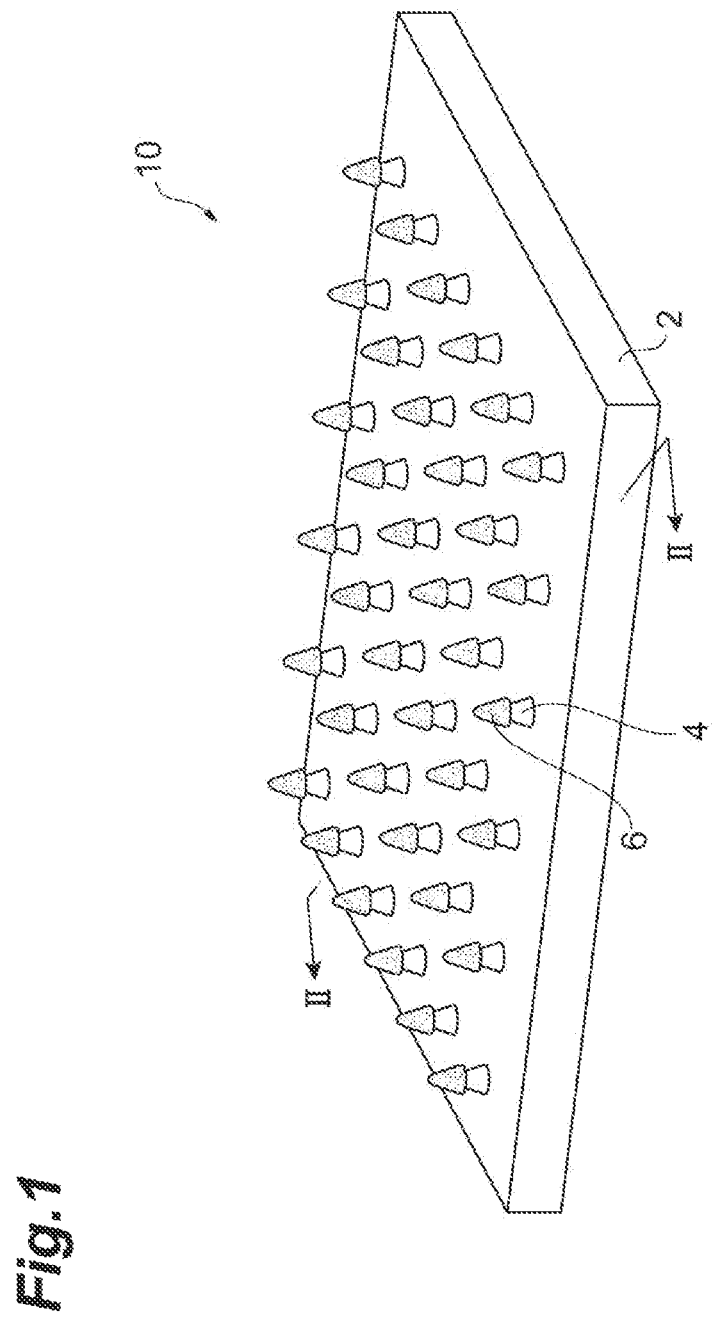
FIG. 1 is a perspective view showing a microneedle device in an embodiment.
Figure 2:
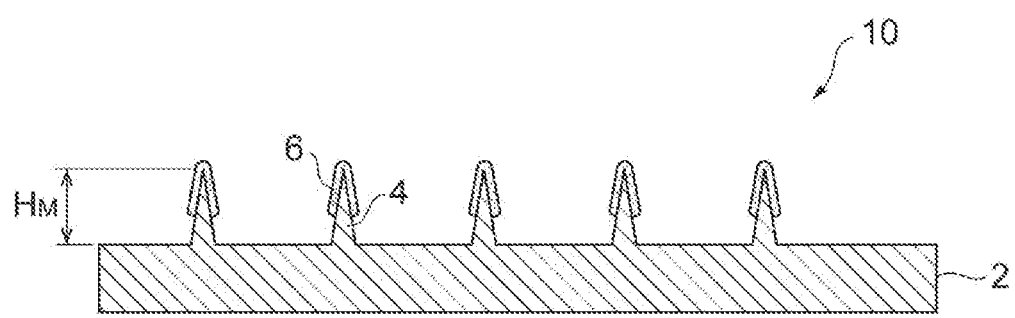
FIG. 2 is a cross-sectional view taken from line II-II of FIG. 1.

The microneedle device of the present invention comprises a substrate, microneedles disposed on the substrate, and a coating layer formed on the microneedles. The microneedle device of the present invention in an embodiment is shown in FIG. 1 and FIG. 2. A microneedle device 10 comprises a substrate 2, a plurality of microneedles 4 disposed on the surface of the substrate 2, and a coating layer 6 formed on the microneedles 4. In the present specification, a structure having microneedles 4 formed on the substrate 2 is referred to as a microneedle array. The detail of the microneedle array is as follows.

The substrate 2 is a foundation for supporting the microneedles 4. The shape and the form of the substrate 2 are not particularly limited, and are, for example, a rectangular shape or a circular shape and a flat form or a curved form. The area of the substrate 2 is, for example, 0.5 to 10 cm$^2$, or 1 to 3 cm$^2$.

The microneedle 4 is a convex structure, which denotes a needle shape in a broad sense or a structure comprising a needle shape. The microneedle 4 is not limited to a structure having a needle shape with a pointed end, and may be in a shape without a pointed end. The microneedle 4 is, for example, in a polygonal pyramid shape such as a quadrangular pyramid shape or a conical shape. The length (height) $H_M$ of the microneedle 4 is 300 to 500 μm, more preferably 400 to 500 μm. The length $H_M$ of the microneedle 4 denotes the height of the microneedle 4 measured in the vertical direction from the surface of the substrate 2 as the reference surface.

Figure 3:
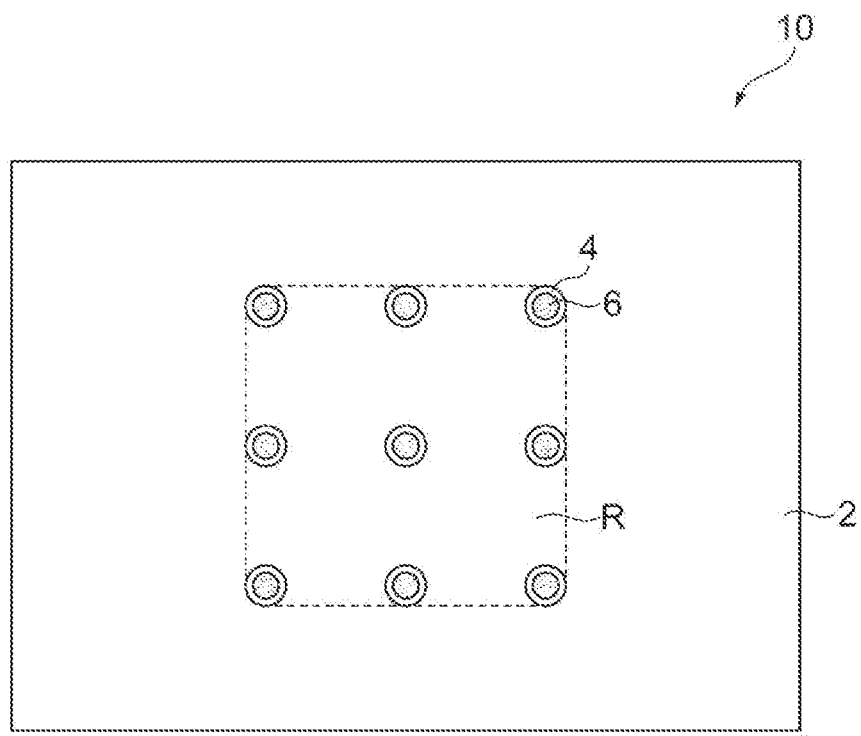
FIG. 3 is a plan view showing a microneedle device in an embodiment.

The microneedles 4 may be arranged in a square lattice form, a rectangular lattice form, an orthorhombic lattice form, a 45-degree staggered form, or a 60-degree staggered form, though not limited thereto. The microneedles 4 may be disposed on the whole of the substrate 2, or may be disposed on some regions of the substrate 2 as shown in FIG. 3.

The microneedles 4 are disposed on the substrate 2 at a density of 28 to 80 needles cm$^2$. From the perspective of reducing skin irritation and administering an effective amount of a biologically active substance, the density of the microneedles 4 on the substrate 2 is preferably 28 to 76 needles/cm$^2$, more preferably 50 to 76 needles/cm$^2$. A microneedle device 10 having such a needle density causes less skin irritation than microneedle devices having the same features except for having a needle density of 156 to 640 needles/cm$^2$. The microneedle devices having the same features mean microneedle devices having a coating layer comprising at least the same amount of the same biologically active substance, with a microneedle length of 300 to 500 μm.

The density of microneedles 4 disposed on the substrate 2 (needle density) is the number of microneedles 4 per unit area in a region substantially equipped with the microneedles 4. The unit is, for example, needles/cm$^2$. The region substantially equipped with the microneedles 4 is a region defined by connecting the outermost microneedles 4 among the microneedles disposed at a microneedle device 10. For example, in the microneedle device 10 shown in FIG. 3, the region substantially equipped with the microneedles 4 is the region R surrounded by a broken line.

Examples of the material of the substrate 2 or the microneedle 4 include silicon, silicon dioxide, ceramics, metals, polysaccharides, and synthesized or natural resin materials. More specifically, biodegradable polymers such as polylactic acid, polyglycolide, polylactic acid-co-polyglycolide, pullulan, caprolactone, polyurethane and polyanhydride, or resin materials such as polycarbonate, polymethacrylate, ethylene vinyl acetate, polytetrafluoroethylene and polyoxymethylene are preferable.

The coating layer 6 may be formed on all of the plurality of microneedles 4 that exist, or may be formed on a part of the microneedles 4 only. The coating layer 6 may be formed on a tip part only of the microneedle 4, or may be formed to cover the whole of the microneedle 4. The average thickness of the coating layer 6 may be less than 50 or may be 1 μm to 30 μm.

The coating layer 6 comprises one or more biologically active substances. The biologically active substances may be low-molecular weight compounds or macromolecules, and may be, for example, vaccines or other proteins, hormones, peptides, or nucleic acids. Specific examples of the biologically active substance include a Japanese encephalitis vaccine, a bacille Calmette-Guerin (BCG) vaccine, ovalbumin (OVA), parathyroid hormone (PTH), and risedronate, as well as pharmaceutically acceptable salts thereof. Particularly, in the case where the biologically active substance to be administered is a Japanese encephalitis vaccine, use of the microneedle device 10 of the present invention is more effective, because the pigmentation caused by the Japanese encephalitis vaccine can be reduced.

The amount of the coating layer 6 depends on the amount of biologically active substance, and it may, for example, be 0.1 to 400 μg or 1 to 300 μg. The amount of the biologically active substance in the coating layer 6 is, for example, 0.1 to 100 μg, although depending on the purpose of treatment and the effective amount of the biologically active substance. As an example, in the case where the biologically active substance is a Japanese encephalitis vaccine, the amount of Japanese encephalitis vaccine per 1 cm² of the substrate 2 may be 0.01 to 10 μg, and is preferably 0.05 to 5 μg, from the perspective of achieving a substantial effect of the Japanese encephalitis vaccine. The amount of Japanese encephalitis vaccine per 1 cm² of the substrate 2 is, for example, 0.2 to 1.2 μg, and from the perspective of reducing pigmentation, it is preferably 0.2 to 0.4 μg. The degree of pigmentation may be determined, for example, by applying the microneedle device 10 to the skin of a dog, peeling the microneedle device 10, and measuring the lightness (L* value) of the skin with a colorimeter after a predetermined period of time (e.g., 40 days). Alternatively, the degree of pigmentation may be evaluated by comparing the lightness of a skin with pigmentation and the lightness of a normal skin without pigmentation, calculating the difference (ΔL* value), and taking the average thereof.

The coating layer 6 may further comprise biologically inactive components (components other than the biologically active substance). The total amount of the biologically inactive components in the whole amount of the coating layer 6 is, for example, 0 mass % to 70 mass %. Examples of the biologically inactive components include a base, a stabilizer, a pH adjuster, and other components (e.g., components for accelerating transfer of drugs into blood, a surfactant, oils and fats, and inorganic substances).

A microneedle device 10 of the present invention may be produced, for example, by applying a coating composition comprising a biologically active substance to microneedles 4 of a microneedle array, and drying the composition to form a coating layer 6 on the microneedles 4. Coating may be performed, for example, by filling a reservoir having multiple hollows with a coating composition, and dipping the microneedles 4 therein.

The coating composition may comprise a solvent (water, polyalcohols, lower alcohols, triacetin, etc.) for dissolving the biologically active substance and other components contained in the coating layer 6. All or a part of the solvent is removed in the step of drying the coating composition.

In preparation of a microneedle device 10 having microneedles 4 with a length $H_M$ of 300 to 500 μm and a coating layer 6 comprising a biologically active substance, the needle density of the microneedle device 10 may be determined by the following method. The method for determining the needle density of the microneedle device 10 may comprise the steps of preparing a microneedle device with microneedles disposed on a substrate at a needle density of 156 to 640 needles/cm², preparing a microneedle device with microneedles disposed on a substrate at a needle density of 28 to 80 needles/cm², and measuring the skin irritation for each of the microneedle devices prepared in the case where the skin irritation caused by the microneedle device having a needle density of 28 to 80 needles/cm² is less than the skin irritation caused by the microneedle device having a needle density of 156 to 640 needles/cm², the density of the microneedle device 10 may be determined to be 28 to 80 needles/cm². Through determination of the needle density by such a method, the microneedle device 10 of the present invention may be obtained.

Preferably, the microneedle device having a needle density of 28 to 80 needles/cm² and the microneedle device having a needle density of 156 to 640 needles/cm² have the same amount of the same biologically active substance. More preferably, the features of the devices other than the needle density are the same. Having the same features except for the needle density means having the same amount of the same biologically active substance, and microneedles with a length of 300 to 500 μm.

The skin irritation caused by a microneedle device may be measured, for example, for an animal subject other than a human, though not limited thereto.

In the present specification, the skin irritation may be indicated, for example, by primary irritation index of Draize Method (P.I.I. value). The P.I.I. value is an index for indicating the degree of irritation of a stimulant, which is used in a skin irritation test by Draize method. The detail of the skin irritation test of a microneedle device by Draize method is as follows.

First, a microneedle device is applied to the shaved dorsal skin of a rabbit for a specified time. At 1, 24 and 48 hours after peeling the microneedle device, changes in the skin irritation (formation of erythema, eschar or edema) are observed and the skin conditions are scored based on the scoring criteria in Table 1.

TABLE 1

| Observation items and degree thereof | Score |
|---|---|
| <Formation of erythema and eschar> | |
| No erythema | 0 |
| Very mild erythema (barely identified) | 1 |
| Distinct erythema | 2 |
| Moderate or severe erythema | 3 |
| From severe erythema (beet redness) to formation of mild eschar (deep damage) | 4 |
| <Formation of edema> | |

TABLE 1-continued

| Observation items and degree thereof | Score |
|---|---|
| No edema | 0 |
| Very mild edema (barely identified) | 1 |
| Mild edema (distinct swelling with clear edge identified) | 2 |
| Moderate edema (about 1-mm swelling) | 3 |
| Severe edema (about 1-mm swelling and spread beyond exposure range) | 4 |

The total of the score from the perspective of erythema and eschar formation and the score from the perspective of edema formation is calculated, and the average of the scores calculated at 1, 24 and 48 hours after peeling the device (primary irritation index) is obtained. In other words, a P.I.I. value is the average of the scores scored in accordance with the scoring criteria of Draize method at 1, 24 and 48 hours after peeling the microneedle device applied to a rabbit.

Although the irritation evaluation using the P.I.I. value is performed, typically based on the following Draize criteria, the evaluation on the skin irritation caused by the microneedle device is not limited to the framework of this criteria. In other words, the skin irritation caused by microneedle devices may be evaluated by comparison of the respective P.I.I. values of different microneedle devices. It can be said that the lower the P.I.I value of a microneedle device is, the less the skin irritation caused by the device is. The microneedle device 10 of the present invention may have a P.I.I. value less than half the P.I.I. value of a microneedle device with microneedles disposed on the substrate at a density of 156 to 640 needles/cm$^2$. The P.I.I. value of a microneedle device may be used in a method for determining the needle density of the microneedle device 10.

<Draize Criteria>
P.I.I.=0: non-stimulant
0<P.I.I.<2: mild stimulant
2≤P.I.I.<5: moderate stimulant
5≤P.I.I.: severe stimulant The microneedle device 10 of the present invention is usually applied to the skin of a subject to be treated such as a patient for a specified period of time. The period of time for application of the microneedle device 10 is different depending on the biologically active substance. In the case where the biologically active substance is a Japanese encephalitis vaccine, the period of time of application of the microneedle device 10 is, for example, 10 seconds to 5 minutes.

EXAMPLES

The microneedle devices having features shown in Table 2 to Table 7 were prepared. Each microneedle has a coating layer comprising an agent. Using these microneedle devices, a skin irritation test was performed in accordance with Draize method. The details are as follows. A microneedle device was applied to the shaved dorsal skin of a test animal for 5 minutes. The P.I.I. value of each device was calculated from the conditions of the skin at 1, 24 and 48 hours after peeling the microneedle device. The details of the test animal are as follows.

<Test Animal>
Animal species (strain)/sex: rabbit (Japanese White species (JW), Specific pathogen free (SPF))/female
Age in weeks when brought in: 17 to 22 week-old (19 to 24 week-old when used)
Number of animals used/number of animals brought in: 6 animals/10 animals
Supply source: Kitayama Labes Co., Ltd.

TABLE 2

| | Agent | Amount of agent (μg) | Length of needle (μm) | Needle density needles/cm$^2$ | Area (cm$^2$) | PII value |
|---|---|---|---|---|---|---|
| Comparative Example 1-1 | Japanese encephalitis vaccine | 0.1 | 500 | 640 | 1 | 0.87 |
| Comparative Example 1-2 | Japanese encephalitis vaccine | 0.8 | 500 | 156 | 1 | 0.33 |
| Example 1-1 | Japanese encephalitis vaccine | 0.8 | 500 | 76 | 1 | 0.13 |
| Example 1-2 | Japanese encephalitis vaccine | 0.8 | 500 | 52 | 1 | 0.07 |

TABLE 3

| | Agent | Amount of agent (μg) | Length of needle (μm) | Needle density needles/cm$^2$ | Area (cm$^2$) | PII value |
|---|---|---|---|---|---|---|
| Comparative Example 1-3 | Japanese encephalitis vaccine | 1.2 | 500 | 156 | 1 | 0.2 |
| Example 1-3 | Japanese encephalitis vaccine | 1.2 | 500 | 52 | 1 | 0.07 |
| Example 1-4 | Japanese encephalitis vaccine | 1.2 | 500 | 28 | 1 | 0 |

TABLE 4

| | Agent | Amount of agent (μg) | Length of needle (μm) | Needle density needles/cm$^2$ | Area (cm$^2$) | PII value |
|---|---|---|---|---|---|---|
| Comparative Example 2 | PTH | 15 | 500 | 640 | 1 | 1.67 |
| Example 2 | PTH | 15 | 500 | 52 | 1 | 0.78 |

TABLE 5

| | Agent | Amount of agent (μg) | Length of needle (μm) | Needle density (needles/cm$^2$) | Area (cm$^2$) | PII value |
|---|---|---|---|---|---|---|
| Comparative Example 3-1 | Risedronate | 20 | 500 | 640 | 1 | 2.33 |
| Comparative Example 3-2 | Risedronate | 20 | 500 | 156 | 1 | 2.22 |
| Example 3-1 | Risedronate | 20 | 500 | 76 | 1 | 1.11 |
| Example 3-2 | Risedronate | 20 | 500 | 52 | 1 | 1 |
| Example 3-3 | Risedronate | 20 | 500 | 2 | 1 | 0.78 |

TABLE 6

| | Agent | Amount of agent (μg) | Length of needle (μm) | Needle density (needles/cm²) | Area (cm²) | PII value |
|---|---|---|---|---|---|---|
| Comparative Example 4-1 | BCG vaccine | 13 | 500 | 640 | 1 | 4.22 |
| Comparative Example 4-2 | BCG vaccine | 13 | 500 | 156 | 1 | 4 |
| Example 4-1 | BCG vaccine | 13 | 500 | 76 | 1 | 2.78 |
| Example 4-2 | BCG vaccine | 13 | 500 | 52 | 1 | 2.11 |
| Example 4-3 | BCG vaccine | 13 | 500 | 28 | 1 | 1.33 |

TABLE 7

| | Agent | Amount of agent (μg) | Length of needle (μm) | Needle density (needles/cm²) | Area (cm²) | PII value |
|---|---|---|---|---|---|---|
| Comparative Example 5 | OVA | 15 | 500 | 640 | 1 | 2 |
| Example 5 | OVA | 15 | 500 | 52 | 1 | 0.44 |

The results of irritation tests are shown in Table 2 to Table 7. With use of any of the agents, the P.I.I. values of the microneedle devices having a needle density of 28 to 80 needles cm² were lower than the values of the microneedle devices having a higher needle density. This means that with use of the microneedle device having a needle density of 28 to 80 needles/cm², the skin irritation caused by the administration of various agents was reduced.

Next, the skin irritation caused by the microneedle device was checked using 6 female beagle dogs as follows. The microneedle devices having the features shown in Table 8 were prepared. Each microneedle has a coating layer comprising a Japanese encephalitis vaccine. Each of the microneedle devices was applied to the shaved dorsal skin of a dog for 5 minutes. The skin conditions at 1, 3, 6, 9 and 15 days after peeling the microneedle device were scored in accordance with the scoring criteria of Draize method. The average of the scores was calculated and the average was regarded as the P.I.I. value of each device according to Draize method. Further, in the case where pigmentation was found 40 days after peeling the device, the lightness (L* value) of the skin was measured with a colorimeter. The lightness of the skin with pigmentation and the lightness of the normal skin without pigmentation were compared to calculate the difference (ΔL* value), of which average was taken to evaluate the degree of pigmentation. As the colorimeter, a portable colorimeter TCD100 (manufactured by Beijing TIME High Technology Co., Ltd.) was used.

TABLE 8

| | Amount of vaccine (μg) | Length of needle (μm) | Needle density (needles/cm²) | Area (cm²) | PII value | Number of cases of pigmentation | Lightness of skin (ΔL*) |
|---|---|---|---|---|---|---|---|
| Comparative Example 6-1 | 0.1 | 500 | 640 | 1 | 1.2 | 5 | 3.2 |
| Comparative Example 6-2 | 0.4 | 500 | 640 | 1 | 1.8 | 6 | 6.8 |
| Comparative Example 6-3 | 2 | 500 | 640 | 1 | 3 | 6 | 9.3 |
| Example 6-1 | 0.4 | 500 | 28 | 1 | 0.8 | 2 | 1.1 |
| Example 6-2 | 0.2 | 500 | 52 | 1 | 0.9 | 3 | 1.8 |
| Example 6-3 | 0.4 | 500 | 52 | 1 | 0.8 | 3 | 1.8 |
| Example 6-4 | 0.4 | 500 | 76 | 1 | 1.2 | 3 | 2.9 |

The results of the irritation test are shown in Table 8. As with the skin irritation test using rabbits, the P.I.I. values of the microneedle devices having a needle density of 28 to 80 needles/cm² were lower than the P.I.I. values of the microneedle devices having a higher needle density. The incidence and the degree of pigmentation were correlated with the skin irritation (P.I.I. value) of microneedle devices. In Examples with use of a microneedle device having a needle density of 28 to 80 needles/cm², the incidence of pigmentation and the degree of pigmentation were low.

REFERENCE SIGNS LIST

2: substrate, 4: microneedle, 6: coating layer, 10: microneedle device, $H_M$: length of microneedle

The invention claimed is:

1. A microneedle device comprising:
   a substrate;
   microneedles disposed on the substrate; and
   a coating layer formed on the microneedles,
   wherein a length of the microneedles is 300 to 500 μm,
   the microneedles are disposed on the substrate at a density of 28 to 80 microneedles/cm², and
   the coating layer comprises a biologically active substance comprising Japanese encephalitis vaccine.

2. The microneedle device according to claim 1, designed for causing less skin irritation than microneedle devices having microneedles disposed on a substrate at a density of 156 to 640 microneedles/cm².

3. The microneedle device according to claim 2, wherein the skin irritation is indicated by a primary irritation index of Draize method.

* * * * *